United States Patent [19] [11] 3,959,470
Mashkovsky et al. [45] May 25, 1976

[54] PSYCHOTROPIC MEDICINAL PREPARATION

[76] Inventors: Mikhail Davidovich Mashkovsky, Leningradsky prospekt, 75a, kv. 55; Robert Georgievich Glushkov, ulitsa Gorkogo, 43, kv. 90; Natalia Ivanovna Andreeva, Frunzenskaya Naberzhnaya, 54, kv. 8; Anatoly Boleslavovich Smulevich, Chernomorsky bulvar, 23, korpus 1, kv. 63; Grigory Yakovlevich Avrutsky, ulitsa Junykh Lenintsev, 102, kv. 36; Valentina Vasilievna Gromova, ulitsa Dubininskaya, 11/17, kv. 183, all of Moscow, U.S.S.R.

[22] Filed: Mar. 10, 1975

[21] Appl. No.: 557,189

Related U.S. Application Data

[63] Continuation of Ser. No. 415,170, Nov. 12, 1973, abandoned.

[30] Foreign Application Priority Data

Nov. 28, 1972 U.S.S.R. .............................. 1850615

[52] U.S. Cl. .................... 424/250; 260/250 BN; 260/268 PC

[51] Int. Cl.$^2$ ......................................... A61K 31/495
[58] Field of Search ............. 424/250; 260/250 BN, 260/268 PC

[56] References Cited
UNITED STATES PATENTS 3,468,890   9/1969   Archer .......................... 260/268 PC

*Primary Examiner*—Stanley J. Friedman
*Attorney, Agent, or Firm*—Holman & Stern

[57] ABSTRACT

A psychotropic medicinal preparation comprising a therapeutically effective amount of an active principle which is a salt of 3-methyl-8-methoxy-3H, 1,2,5,6-tetrahydropyrazino-[1,2,3]-ab-$\beta$-carbolin, and a pharmaceutical carrier therefor.

The medicinal preparation is employed in the form of tablets or solutions, the amount of the active principle being 0.025 gm in the tablets and 0.0125 to 0.025 gm in the solutions.

The medicinal preparation of the invention is designed for the treatment of depressions and other psychic disorders.

7 Claims, No Drawings

PSYCHOTROPIC MEDICINAL PREPARATION

This is a continuation, of application Ser. No. 415,170, filed Nov. 12, 1973, now abandoned.

The present invention relates to a psychotropic medicinal preparation for the treatment of depressions and other psychic disorders.

At present there exist a great range of psychotropic and, inter alia, antidepressant, medicinal preparations such as Decipramine, Imipramine, etc. The known medicinal preparations, however along with a marked therapeutic effect, produce some side effects, such as dryness in the mouth, constipation, accomodation disturbances, etc., which limit their application for certain categories of patients.

It is an object of the present invention to provide a novel psychotropic medicinal preparation which would equal the known preparations in effectiveness but would produce fewer side effects.

The object of this invention is attained by providing a psychotropic medicinal preparation which comprises, in accordance with the invention, a therapeutically effective amount of the active principle which is a salt of 3-methyl-8-methoxy-3H, 1, 2, 5, 6, - tetrahydropyrazinn - [1,2,3,-ab]-β - carbolin

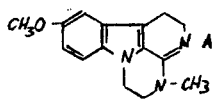

where A is an organic or inorganic acid.

The hydrochloride of said preparation was given a provisional name "Incazan" and is prepared by the cyclization of 9-[β-N,N-dimethylamino)]-ethyl-6-methoxy-1-oxo-1,2,3,4-tetrahydro-β-carbolin hydrochloride with phosphorus oxychloride while heating as taught in copending application Ser. No. 415,841 filed on Nov. 14, 1973.

The medicinal preparation of this invention is an odourless white powder with a yellowish tint, bitter of taste, freely soluble in water, having a molecular weight of 291.5 and a melting point of 305° to 308°C.

The bitartrate semihydrate of said compound is prepared according to the method of U.S. patent application Ser. No. 43,143, filed Nov. 14, 1973 in the names of Robert G. Glushkov, et al., as slightly yellowish crystals freely soluble in water, having a molecular weight of 339 and a melting point of 220° to 222°C.

For administration per os, the medicinal preparation is manufactured in the form of tablets, wherein the carrier is a pharmaceutical filler, such as lactose, starch and calcium stearate. The amount of the active principle in the tablets is 0.025 gm.

For parenteral administration, the recommended form comprises as the carrier a pharmaceutical solvent, for example water for injections. In this form the amount of the active principle is 0.0125 to 0.025 gm, with the aqueous solution employed having a concentration of 1.25 percent.

The pharmacological properties of the hydrochloride of said medicinal preparation (Incazan) and of its other salts, such as bitartrate semihydrate, are the same as those of other antidepressants. The proposed medicinal preparation promotes the central effect of amphetamine and 5-hydroxytriptophane, and the peripheral effects of adrenaline, phenylethylamine, tyramine, serotonine and tryptamine.

The proposed medicinal preparation mitigates the depressing effects of reserpine and tetravenazine as well as the cataleptic activity of phenotiazine derivatives (meterazine). Along with some features characterizing the known antidepressants (Imipramine, Decipramine, etc.), the proposed medicinal preparation also possesses some distinctive characteristics. Thus, it produces no cholinolithic effect; nor does it promote the soporific effect of Hexenal, or the analgesic effect of Promedol, or the local-anaesthetic activity of Novocaine.

The proposed medicinal preparation excels Impipramine in promoting the effects of phenylethylamine, tyramine and tryptamine Biochemical investigations indicate that the proposed medicinal preparation administered in doses sufficing to produce a marked therapeutic effect moderately inhibits monoaminosidase activity only in the tissues of the kidneys, which gives reasons to believe that its pharmacological effect is not based on antimonoaminoxidase action.

The toxicity of the medicinal preparation of this invention is quite low. Thus, the $LD_{50}$ of the medicinal preparation administered per os to mice is 445 mgm/kg.

The toxicological investigations of the proposed medicinal preparation on mice, rats and rabbits using single and multiple (during one month) doses have revealed that in amounts exceeding the clinically recommended doses by 30 to 50 times the medicinal preparation has no toxic effect on the animals.

The proposed medicinal preparation was tested in the treatment of depressive states on 46 patients (13 men and 33 women). 33 Patients were hospitalized and 13 were treated as outpatients. The age structure of the group as of the time of treatment was as follows: 2 patients below 21 years of age; 20 patients from 21 to 30; 10 patients from 31 to 40; 11 patients from 41 to 50; and 3 patients above 50. By nosological froms, the patients were classified as follows:

1. schizophrenia — 40 subjects
   including recurrent — 1.
              shift-like — 30
              sluggish — 9;
2. maniac-depression psychosis — 4 subjects; and
3. reactive depressions — 2 subjects The preparation was given in 25-mgm tablets once or twice a day (in the morning and evening). The average daily dose was from 25 mgm depending on the depth and structure of a particular depression. The duration of the course was from 1–2 weeks to 4 months.

As a result of the treatment, depression symptoms totally disappeared in 14 patients and were mitigated in another 18 patients. The therapeutic effect was the greatest in the patients whose depressive symptoms were associated with the disturbances of the anergic pole. The proposed preparation also proved effective in neurotic and hypochondriac depressions as well as in shallow depressions with delirium of depressive contents.

The Patients with auxions depression were given the proposed preparation in small doses, 25 to 50 mgm per day (since large doses intensified the state of anxiety) in combination with sedatives, such as Triphthazine, Sonapax, etc.

The side effects of the proposed medicinal preparation were as follows: agitated depression – 1 case; intensified anxiety and anxious fobics – 3 cases; dermatitis – 2 cases; headache – 1 case. It should be noted that headache and dermatitis were transitory (without the preparation being withdrawn).

The clinical study of the proposed medicinal preparation has led to the conclusion that Incazan is an antidepressant recommendable for the treatment of sluggish, apathetic, adynamic, neurotic hypochondriac and other depressive states.

Since it produces few side effects, the proposed medicinal preparation may be recommended for the treatment of both hospitalized patients and outpatients. The proposed medicinal preparation may be used in combination with neuroleptics, such as Triphthazine, Itaperazine, Sonapax, etc.

What is claimed is:

1. A psychotropic medicinal preparation comprising a therapeutically effective amount of an active principle which is a salt of 3-methyl-8-methoxy-3H,1,2,5,6-tetrahydropyrazino-[1,2,3]-ab- -carbolin of the following formula:

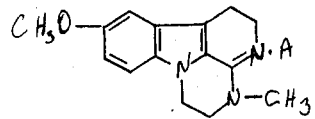

where A is an inorganic or organic acid, and a pharmaceutical carrier selected from the group consisting of pharmaceutical fillers and solvents for injections.

2. A medicinal preparation as claimed in claim 1, wherein said carrier is a pharmaceutical filler and said preparation is in the form of tablets.

3. A medicinal preparation as claimed in claim 2, wherein the filler is lactose, starch or calcium stearate.

4. A medicinal preparation as claimed in claim 2, which comprises 0.025 gm of the active principle.

5. A medicinal preparation as claimed in claim 1, wherein the carrier is a solvent for injections.

6. A medicinal preparation as claimed in claim 5, wherein the solvent is water.

7. A medicinal preparation as claimed in claim 5, which comprises 0.0125 to 0.025 gm of the active principle.

* * * * *